United States Patent [19]

Arcas et al.

[11] Patent Number: 5,377,546
[45] Date of Patent: Jan. 3, 1995

[54] MULTI-DEGREE LINEAR LINER IMPEDANCE TESTING DEVICE

[75] Inventors: Noe Arcas, Plainview; Shepard G. Kay, North Bellmore; Charles A. Parente, Oyster Bay, all of N.Y.

[73] Assignee: Grumman Aerospace Corporation, Bethpage, N.Y.

[21] Appl. No.: 827,606

[22] Filed: Jan. 29, 1992

[51] Int. Cl.6 .............................................. G01N 29/00
[52] U.S. Cl. ............................................ 73/589; 73/588
[58] Field of Search ................. 73/589, 584, 588, 599, 73/583, 579

[56] References Cited

U.S. PATENT DOCUMENTS

| | | | |
|---|---|---|---|
| 2,981,096 | 12/1956 | Carrell | 73/589 |
| 4,305,295 | 12/1981 | Andersson et al. | 73/589 |
| 4,397,187 | 8/1983 | Stribling | 73/589 |
| 4,537,630 | 8/1985 | Syed | 73/589 |
| 4,651,566 | 3/1987 | Andersson et al. | 73/589 |
| 4,768,379 | 9/1988 | Arcas et al. | 73/589 |

Primary Examiner—Hezron E. Williams
Assistant Examiner—Nashmiya Ashraf
Attorney, Agent, or Firm—Bacon & Thomas

[57] ABSTRACT

A device for permitting evaluation of the acoustic impedance of liner designs used to attenuate noise in engine aircraft inlet and exhaust ducts, and in particular multiple degree of freedom designs of the type which include a porous facesheet followed by a backing depth followed by successive facesheet/backing depth combinations, includes a plurality of spacers of different thicknesses for varying the backing depths, and a movable plunger with a threaded adjustment mechanism for establishing the final backing depth. Gaskets and seals are installed at various interfaces to eliminate noise leakage paths. Two attachment bolts are used to hold the plunger assembly, face sheets, and spacers together, and an alignment disc positioned on the first facesheet is used to properly align an impedance tube waveguide on facesheet.

22 Claims, 2 Drawing Sheets

MULTI-DEGREE LINEAR LINER IMPEDANCE TESTING DEVICE

BACKGROUND OF THE INVENTION

1. Field of the Invention

This invention relates to a device for testing multiple degree of freedom noise attenuation structures, and in particular to a device for testing the acoustic impedance of liner designs used to attenuate noise in engine aircraft inlet and exhaust ducts.

2. Description of Related Art

Acoustic liners and similar structures used to attenuate noise in, for example, engine aircraft inlet and exhaust ducts, are conventionally formed of a solid backface and one or more perforate facesheets separated by a core structure. The core structure defines the distance between the backface and the facesheets without significantly affecting the acoustic properties of the liner.

FIG. 1 shows one such liner configuration. Liner 1 is defined as a two degree of freedom configuration because it includes two respective facesheets 2 and 3. Spacing between facesheets 2 and 3 and solid backface 4 is provided by respective cores 5 and 6.

The different spacings between the facesheets 2 and 3 and the backface 4 cause the structure to attenuate different frequencies. In the example shown, because two facesheets at two different spacings are provided, multiple frequencies of noise can be attenuated. The more facesheets or "degrees of freedom" possessed by the liner, the greater the range of acoustic frequencies attenuate.

A variety of different facesheet and core configurations are presently in use. One type of conventional liner includes a stainless steel mesh supported by an open weave perforate graphite/epoxy backface, a non-metallic core, and a structural laminate graphite/epoxy backface. A second type of known liner includes an aluminum hex core, corrosion-resistant wire mesh supported by a microporous or aluminum perforated facesheet, and a solid non-porous backface.

In order to evaluate the acoustic properties of this type of liner design, it is conventional to fabricate test samples consisting of facesheets separated by honeycomb cores of different thicknesses in order to provide varied backing depths. These samples are then tested with an acoustic impedance measurement device such as the one disclosed in U.S. Pat. No. 4,768,379. However, for each liner design evaluated, only a fixed set of face sheet/depth configurations can be tested using the conventional measurement device. In order to obtain an optimum configuration, numerous different samples must be manufactured for testing. This significantly increases the cost and time needed to design a particular multiple degree of freedom liner.

The advantages of multiple degree of freedom acoustic impedance structures include improved attenuating properties and the capability of being tuned for two or more discrete frequencies. However, these advantages are currently offset, at least partially, by the disadvantage described above that a large amount of testing is required to verify and fine tune such designs. As a result, it would be highly desirable to provide an acoustic impedance testing device in which different facesheets and depth or spacing combinations could be easily tested without the need for fabricating a different test sample for each combination to be tested.

SUMMARY OF THE INVENTION

It is an objective of the invention to provide a mechanism for testing multiple degree of freedom acoustic impedance devices without requiring a separate sample to be manufactured for each fixed set of face sheet/depth configurations to be evaluated. This objective is achieved by providing an apparatus for testing multiple degree of freedom linear liner impedance devices which includes a spacer assembly for variably spacing an arbitrary number of perforated or air passage facesheets with respect to a plunger. The spacers and facesheets are held together by a removable clamping assembly, thereby permitting a facesheet backing depth combinations to be tested by varying the thickness of the spacers rather than by manufacturing entire liners of different thicknesses. The plunger simulates a solid backface, the position of which is variably controlled, for example by a threaded nut and bolt assembly.

The apparatus of the invention may be used in conjunction with an impedance tube of the type disclosed in U.S. Pat. No. 4,768,379. The known impedance tube includes a tube wave guide with an acoustic speaker attached to one end. Microphones, positioned within the sidewalls of the wave guide are used to measure the acoustic pressures in the waveguide which are generated by the acoustic speaker. If the open end of the waveguide is positioned against the first facesheet of the liner, the sound field in the waveguide can be used to determine the impedance, a basic acoustic property, of the liner. Preferably, the preferred testing apparatus includes a built-in guide for positioning the impedance tube with respect to the spaced facesheets and plunger.

DETAILED DESCRIPTION OF THE PREFERRED EMBODIMENTS

Figure 1:
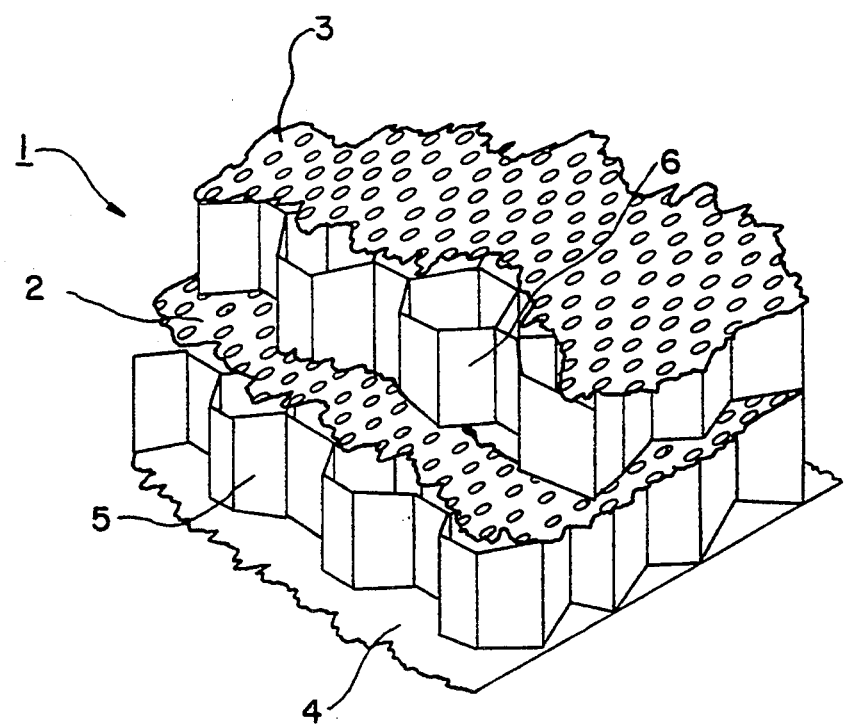
FIG. 1 is a cutaway perspective view of a conventional liner design of the type used to attenuate noise in engine aircraft inlet and exhaust ducts.
Figure 2:
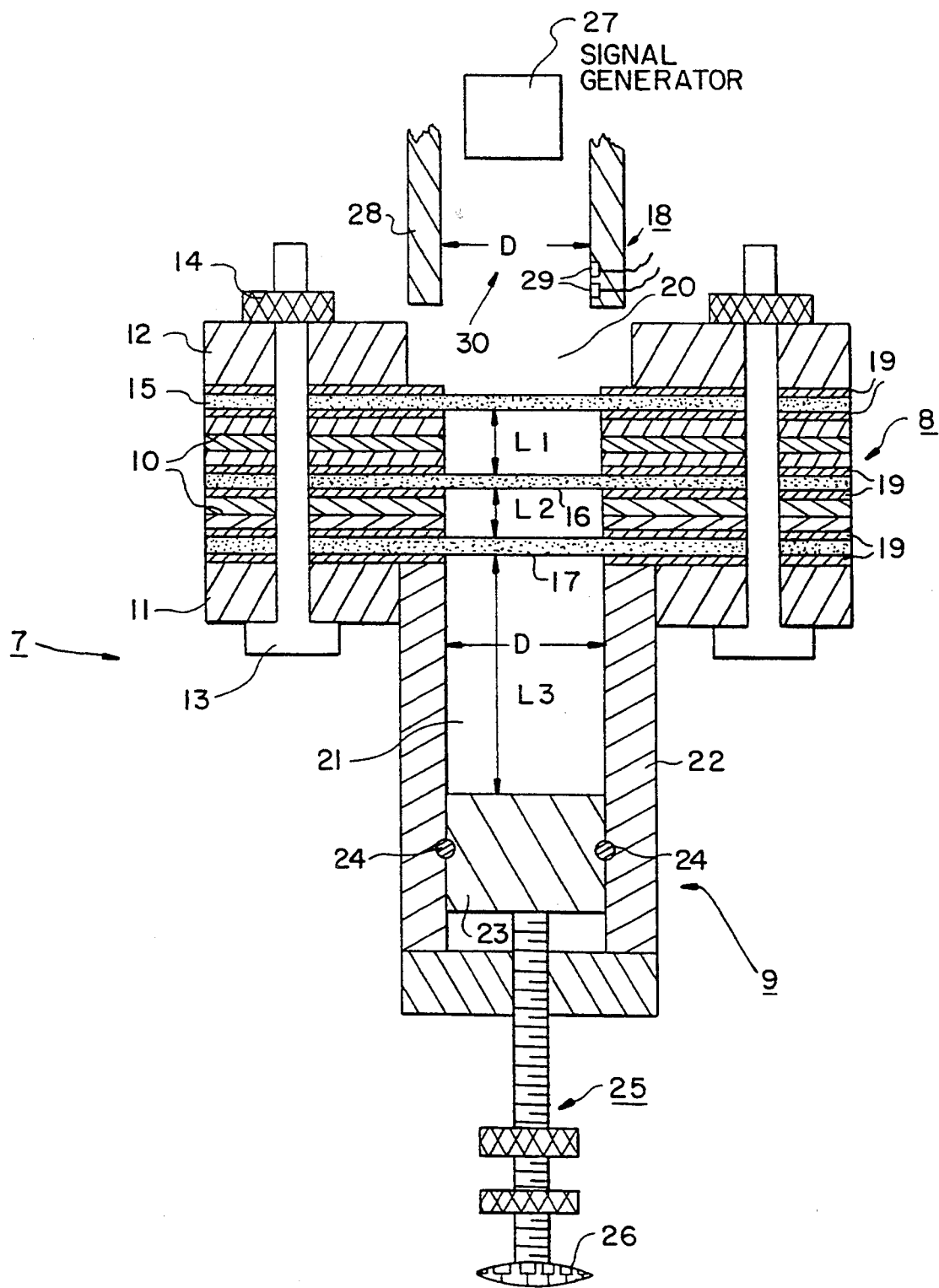
FIG. 2 is a cross sectional side view of an impedance testing apparatus assembled in accordance with the principles of a preferred embodiment of the invention.

FIG. 2 illustrates a testing device 7 assembled in accordance with the particulars of a preferred embodiment of the invention. Testing device 7 includes a facesheet mounting section 8 and a plunger mounting section 9. Facesheet mounting section 8 includes a plurality of annular spacers 10, an annular clamping member 11, an annular alignment member 12, at least one and preferably two clamping bolts 13, and a nut 14. The three facesheets 15–17 are separated at respective distances L1 and L2 by the spacers 10, while alignment member 12 serves to align an impedance tube 18, described in more detail below, with respect to the first facesheet 15. Bolts 13 are inserted through aligned openings in spacers 10, and clamping and alignment members 11 and 12. In addition, annular gaskets 19 having appropriate openings for bolts 13 are provided around each facesheet to prevent noise leakage.

In the preferred embodiment shown, the spacers may be composed of equal width sections, the number of sections determining the respective distances L1 and L2 between facesheets, or the spacers may simply have different thicknesses. Although three facesheets 15–17 are illustrated, the number of facesheets can be increased by simply adding more spacers, and by adjusting the length of clamping bolts 13 as necessary. Further, it will be appreciated by those skilled in the art that the facesheet and spacer assembly 8 may be secured together by means other than a bolt and nut, for example by an external clamp, and that spacers 10 and members 11, 12, and 19 need not necessarily be annular, but rather may assume a variety of shapes, so long as a central aperture 20 is provided for permitting access to the facesheets being tested.

Plunger mounting section 9 is secured at an upper end to clamping member 11 by any suitable means, and may even be integral therewith. A central bore 21 provided in cylindrical main body 22 of plunger mounting section 9 has a width D approximately equal to that of plunger 23. Between the inner wall of cylinder 22 and the plunger is a plunger seal 24.

The plunger 23 is provided to simulate a liner backface and is adjustable to an infinite number of backface to facesheet spacings L3. Adjustment is carried out via a threaded bolt and nut combination 25 threaded through the base of cylinder 22 and illustrated as including a turning knob 26 for convenience. Of course, details of the plunger positioning or adjustment mechanism may be varied in numerous ways by those skilled in the art and still fall within the scope of the invention.

A suitable material for the spacers 10, clamp member 11, alignment member or disc 12, and cylinder 22 is brass. The plunger 23 may also be constructed of brass. Brass is preferred because it has a high density and reduces transmitted noise through the side holes. The gaskets and seals installed at the various interfaces to eliminate noise leakage paths are preferably made of rubber or a similar resilient material. On the other hand, it will be appreciated that numerous other materials may be substituted without departing from the spirit and scope of the invention.

As noted above, testing apparatus 7 may be used in conjunction with an impedance tube 18, which may be of the type disclosed in U.S. Pat. No. 4,768,379, herein incorporated by reference. The impedance tube disclosed in U.S. Pat. No. 4,768,379 includes a tube waveguide 28 with an acoustic signal generator or speaker 27 attached to one end and shown schematically in FIG. 2. Microphones 29, positioned within the sidewalls of the waveguide 28, are used to measure the acoustic pressures in the waveguide which are generated by the acoustic signal generator 27. If the open end 30 of the waveguide is positioned against the first facesheet 15, the sound field in the waveguide can be used to determine the impedance of the liner.

To ensure alignment and proper acoustic sealing between impedance tube 18 and facesheets 15-17, the inner diameter of alignment member 12 is preferably approximately equal to the outer diameter of tube 18, although space may be provided to accommodate a gasket seal between tube 18 and member 12.

Having thus described in detail a preferred embodiment of the invention, many modifications will undoubtedly occur to those skilled in the art. It is therefore desired that the protection afforded by the Letters Patent be limited only by the true scope of the appended claims.

We claim:

1. Apparatus for evaluation of the acoustic impedance of structural members, comprising:
    spacer means for separating at least two of said structural members by a predetermined distance;
    alignment means for aligning an impedance tube with respect to said structural members;
    means for acoustically sealing said apparatus device such that acoustic signals generated within said impedance tube are directed onto said structural members.

2. Apparatus as claimed in claim 1, further comprising a plunger situated a predetermined distance from said structural members on a side of said structural members opposite said impedance tube, and plunger adjustment means for adjusting the distance between said plunger member and said structural members.

3. Apparatus as claimed in claim 2, wherein said plunger adjustment means comprises a threaded adjustment member.

4. Apparatus as claimed in claim 3, wherein said plunger is constructed of an acoustically non-porous material and said structural members are acoustic liner facesheets, whereby said plunger simulates an acoustic liner backface.

5. Apparatus as claimed in claim 1 wherein said spacer means comprises a plurality of spacer members positioned between said structural members, the number and width of said spacer members determining the distance between said structural members.

6. Apparatus as claimed in claim 5, wherein said spacer members are annular.

7. Apparatus as claimed in claim 5, wherein said acoustic sealing means comprises gaskets positioned between said structural members and said spacer members.

8. Apparatus as claimed in claim 1, wherein said alignment means comprises an impedance tube alignment disc having a central aperture dimensioned to fit said impedance tube.

9. Apparatus as claimed in claim 8, further comprising a clamping member and clamping means for releasably clamping together said clamping member, structural members, spacer members, and impedance tube alignment disc.

10. Apparatus as claimed in claim 9, wherein said clamping means comprises a clamping bolt and nut.

11. Apparatus as claimed in claim 9, wherein said acoustic sealing means comprises gasket seals sandwiching each of said structural members.

12. Apparatus as claimed in claim 1, wherein said structural members are acoustic liner facesheets.

13. Apparatus for evaluation of the acoustic impedance of structural members, comprising:
    spacer means for separating at least two of said structural members by a predetermined distance;
    alignment means for aligning an impedance tube with respect to said structural members;
    a plunger situated a predetermined distance from said structural members on a side of said structural members opposite said impedance tube, and plunger adjustment means for adjusting the distance between said plunger member and said structural members.

14. Apparatus as claimed in claim 13, wherein said plunger adjustment means comprises a threaded adjustment member.

15. Apparatus as claimed in claim 13, wherein said plunger is constructed of an acoustically non-porous material and said structural members are acoustic liner face sheets, whereby said plunger simulates an acoustic liner backface.

16. Apparatus as claimed in claim 13, wherein said spacer means comprises a plurality of spacer members positioned between said structural members, the number and width of said spacer members determining the distance between said structural members.

17. Apparatus as claimed in claim 13, wherein said spacer members are annular.

18. Apparatus as claimed in claim 13, further comprising gasket seals positioned between said structural members and said spacer members.

19. Apparatus as claimed in claim 13, wherein said alignment means comprises an impedance tube alignment disc having a central aperture dimensioned to fit said impedance tube.

20. Apparatus as claimed in claim 13, further comprising a clamping member and clamping means for releasably clamping together said clamping member, structural members, spacer members, and impedance tube alignment disc.

21. Apparatus as claimed in claim 13, wherein said clamping means comprises a clamping bolt and nut.

22. Apparatus as claimed in claim 13, further comprising gasket seals sandwiching each of said structural members.

* * * * *